(12) United States Patent
Staveley

(10) Patent No.: US 10,431,115 B2
(45) Date of Patent: Oct. 1, 2019

(54) SYSTEMS AND METHODS FOR USING A SMART REFRIGERATOR TO IMPLEMENT ACCOUNTABILITY MEASURES ASSOCIATED WITH INTAKE OBJECTIVES

(71) Applicant: MasterCard International Incorporated, Purchase, NY (US)

(72) Inventor: Alex Staveley, Dublin (IE)

(73) Assignee: MASTERCARD INTERNATIONAL INCORPORATION, Purchase, NY (US)

( * ) Notice: Subject to any disclaimer, the term of this patent is extended or adjusted under 35 U.S.C. 154(b) by 155 days.

(21) Appl. No.: 15/240,130

(22) Filed: Aug. 18, 2016

(65) Prior Publication Data
US 2018/0053440 A1    Feb. 22, 2018

(51) Int. Cl.
G09B 19/00 (2006.01)
G06Q 30/06 (2012.01)
G16H 20/60 (2018.01)

(52) U.S. Cl.
CPC ..... *G09B 19/0092* (2013.01); *G06Q 30/0633* (2013.01); *G16H 20/60* (2018.01)

(58) Field of Classification Search
CPC ........... G09B 19/0092; G06Q 30/0631; G06Q 30/0633; F25D 2400/36; F25D 2400/361
See application file for complete search history.

(56) References Cited

U.S. PATENT DOCUMENTS

| | | | |
|---|---|---|---|
| 2003/0171944 A1* | 9/2003 | Fine | G06Q 30/06 705/2 |
| 2008/0019122 A1* | 1/2008 | Kramer | A47G 19/025 362/154 |
| 2008/0195944 A1* | 8/2008 | Lee | F25D 29/00 715/706 |
| 2010/0106515 A1* | 4/2010 | McCoy | G06Q 50/22 705/2 |
| 2010/0280895 A1 | 11/2010 | Mottola | |
| 2011/0040608 A1* | 2/2011 | Cohen | G06Q 30/02 705/14.17 |
| 2011/0218839 A1 | 9/2011 | Shamaiengar | |
| 2013/0067375 A1* | 3/2013 | Kim | F25D 29/00 715/769 |
| 2013/0216982 A1* | 8/2013 | Bennett | G09B 5/00 434/127 |

(Continued)

OTHER PUBLICATIONS

U.S. Appl. No. 14/712,592.

*Primary Examiner* — Peter R Egloff
(74) *Attorney, Agent, or Firm* — Armstrong Teasdale LLP

(57) ABSTRACT

A smart refrigerator including a processor, a memory, and a user interface is described herein. The smart refrigerator is configured to receive user input of a nutritional objective from a user via the user interface, and receive user input of a grocery order including a plurality of grocery items via the user interface. The smart refrigerator is also configured to retrieve nutritional information associated with the plurality of grocery items, and compile a nutritional profile for the user from the retrieved nutritional information. The smart refrigerator is further configured to compare the nutritional profile to the nutritional objective to determine whether the user has met the nutritional objective, and release, when the user has met the nutritional objective, a reward to the user.

20 Claims, 11 Drawing Sheets

(56) References Cited

U.S. PATENT DOCUMENTS

| | | | |
|---|---|---|---|
| 2014/0214590 A1* | 7/2014 | Argue | G06O 30/0631 |
| | | | 705/26.7 |
| 2014/0252091 A1* | 9/2014 | Morse | F25D 29/00 |
| | | | 235/385 |
| 2016/0019629 A1 | 1/2016 | Briancon et al. | |
| 2016/0063532 A1* | 3/2016 | Loeb | G06Q 30/0234 |
| | | | 705/14.25 |
| 2016/0133140 A1* | 5/2016 | King | G06Q 40/12 |
| | | | 434/127 |
| 2017/0169189 A1* | 6/2017 | Belz | G06F 19/3475 |

* cited by examiner

SYSTEMS AND METHODS FOR USING A SMART REFRIGERATOR TO IMPLEMENT ACCOUNTABILITY MEASURES ASSOCIATED WITH INTAKE OBJECTIVES

BACKGROUND

This disclosure relates to consumer health tracking and, more specifically, to consumer health tracking using an intake tracking and reward computing device, such a smart refrigerator, to implement accountability measures associated with user-defined intake objectives.

Consumers are increasingly health conscious, but some consumers may struggle to stay on track with their personal health goals. In particular, healthy eating goals may be difficult to meet, as access to unhealthy food is practically ubiquitous. Some consumers may use various "diary"-style services or programs to manually track their food consumption. The user must enter each and every food they consume in a particular meal or particular day, including the amount of each food consumed, which can be a difficult task to complete accurately. Moreover, many users get tired of the tedious task of entering food into their "food diary," which leads to the user abandoning the use of the service entirely. As such, even when consumers are dedicated to meeting their healthy eating goals, accurately and consistently tracking the nutritional information of food purchases can be a time-consuming and frustrating task. Accordingly, there is a need for a system that implements accountability and reward measures to help consumers meet their nutritional intake objectives.

BRIEF DESCRIPTION OF THE DISCLOSURE

In one aspect, a smart refrigerator is provided. The smart refrigerator includes a processor in communication with a memory and a user interface. The processor is programmed to receive user input of a nutritional objective from a user via the user interface, and receive user input of a grocery order including a plurality of grocery items via the user interface. The processor is also programmed to retrieve nutritional information associated with the plurality of grocery items, and compile a nutritional profile for the user from the retrieved nutritional information. The processor is further configured to compare the nutritional profile to the nutritional objective to determine whether the user has met the nutritional objective, and release, when the user has met the nutritional objective, a reward to the user.

In another aspect, a method for implementing accountability measures associated with nutritional objectives is provided. The method is performed using an intake tracking and reward (ITR) computing device including a processor in communication with a memory and a user interface. The method includes receiving user input of a nutritional objective from a user via the user interface, and receiving user input of a grocery order including a plurality of grocery items via the user interface. The method also includes retrieving nutritional information associated with the plurality of grocery items, and compiling a nutritional profile for the user from the retrieved nutritional information. The method further includes comparing the nutritional profile to the nutritional objective to determine whether the user has met the nutritional objective, and releasing, when the user has met the nutritional objective, a reward to the user.

In yet another aspect, a non-transitory computer-readable storage medium having computer-executable instructions embodied thereon is provided. When executed by an intake tracking and rewards (ITR) computing device including at least one processor coupled to a memory and a user interface, the computer-executable instructions cause the ITR computing device to receive user input of a nutritional objective from a user via the user interface, and receive user input of a grocery order including a plurality of grocery items via the user interface. The computer-executable instructions also cause the ITR computing device to retrieve nutritional information associated with the plurality of grocery items, and compile a nutritional profile for the user from the retrieved nutritional information. The computer-executable instructions further cause the ITR computing device to compare the nutritional profile to the nutritional objective to determine whether the user has met the nutritional objective, and release, when the user has met the nutritional objective, a reward to the user.

BRIEF DESCRIPTION OF THE DRAWINGS

FIG. 1 is a block diagram of an intake objective accountability (IOA) system including an intake tracking and reward (ITR) computing device.

FIG. 2 illustrates an example configuration of a client computing device shown in FIG. 1.

FIG. 3 illustrates an example configuration of a server system shown in FIG. 1.

FIG. 4 is a data flow diagram illustrating the flow of data between various components of the IOA system shown in FIG. 1.

FIG. 5 is a first example screenshot of a software application ("app") on a user interface of the ITR computing device showing setting an intake objective.

FIG. 6 is a second example screenshot of the app shown in FIG. 5, showing setting a user-defined reward for meeting the intake objective.

FIG. 7 is a third example screenshot of the app shown in FIG. 5, showing an order screen.

FIG. 8 is a fourth example screenshot of the app shown in FIG. 5, showing a user's pantry screen.

FIG. 9 is a fifth example screenshot of the app shown in FIG. 5, showing a progress screen.

FIG. 10 is a flowchart of a method for using a smart refrigerator to implement accountability measures associated with intake objectives.

FIG. 11 is a diagram of components of an example computing device that may be used in the IOA system shown in FIG. 1.

Figure 1:
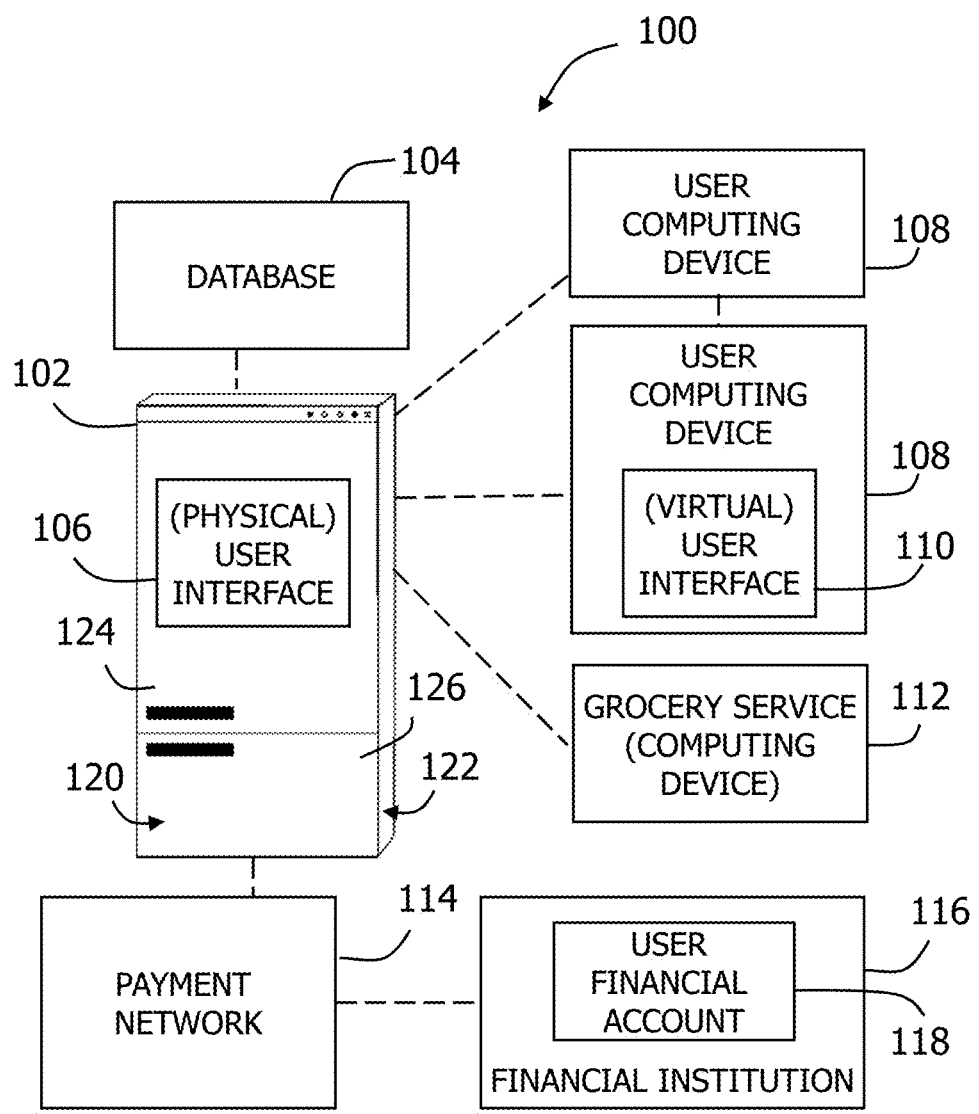
FIGS. 1-11 show example embodiments of the methods and systems described herein.

Like numbers in the Figures indicates the same or functionally similar components. Although specific features of various embodiments may be shown in some figures and not in others, this is for convenience only. Any feature of any figure may be referenced and/or claimed in combination with any feature of any other figure.

DETAILED DESCRIPTION OF THE DISCLOSURE

The intake objective accountability (IOA) system described herein is configured to track a user's grocery or food-related purchases that are made through a user interface, and compare the user's purchases against a user-created nutritional intake objective (referred to herein as "objective," "nutritional objective" and "intake objective," interchangeably). If the user meets the intake objective, the IOA system provides the user with access to a reward. For example, the IOA system releases a predefined reward to the user through the user interface.

In the example embodiment, the IOA system includes an intake tracking and reward (ITR) computing device including and/or in communication with the user interface. The ITR computing device is configured to receive user input of an intake or nutritional objective, track any grocery or food-related purchases made by the user through the user interface, compare the food-related purchases made to the nutritional objective, and release a reward to the user if the user meets the nutritional objective. The ITR computing device may include any computing device configured to function as described herein, including a smart refrigerator, a smartphone, a tablet, a laptop computer, a wearable computing device (e.g., a "smart watch"), a dedicated computing device associated solely with the IOA system, and/or any other computing device. The ITR computing device includes a processor in communication with a memory.

The IOA system further includes a database in wired and/or wireless communication with the ITR computing device. The database is accessible to the ITR computing device and is configured to store and/or otherwise maintain a variety of information, as described further herein. For example, the database may store user intake objectives, user-defined rewards, nutritional information associated with grocery items (i.e., food items), grocery order information, and/or any other information. As used herein, "nutritional information" refers generally to the nutritional content associated with a particular item (e.g., a particular food, recipe, menu item, etc.). Nutritional information may include ingredients as well as information such as caloric content, various vitamins and minerals, and macronutrient levels (e.g., fat, protein, carbohydrates).

The ITR computing device is configured to maintain the user interface for communication between the user and the ITR computing device. In some embodiments, the ITR computing device is configured to execute instructions causing display of a software application ("app") or browser associated with the input and output functionality described herein. In such embodiments, the user may input information to the ITR computing device via the app or browser, as displayed on the user interface. In the example embodiment, the ITR computing device is integral to a smart refrigerator, such that the user interface is both a physical interface mounted on the smart refrigerator and a virtual user interface displayed on the smart refrigerator. It should be understood that, in certain embodiments, the user interface may not be directly mounted to or otherwise physically coupled to the ITR computing device. The physical user interface may be integral to a user computing device (such a smartphone or tablet) "paired with" or otherwise in communication with the ITR computing device, such that the ITR computing device causes display of the app or browser as a virtual user interface on the physical user interface of the user computing device. In other embodiments, the physical user interface may be integral to the smart refrigerator but the ITR computing device including a virtual user interface may be remote therefrom and in wired or wireless communication with the smart refrigerator. In some embodiments, the app is a cloud-based application, such that information associated with the app (e.g., intake objectives, user-defined rewards, user nutritional profiles, nutritional information, etc.) is stored remotely and/or in a cloud environment (e.g., not in one centralized database). Moreover, the app is configured to enable access from a plurality of user computing device(s) to the intake tracking services of the ITR computing device, to make tracking and monitoring the user's progress towards intake objectives and/or grocery ordering more efficient and less burdensome for the user. In some embodiments, the app may have inter-app integration functionality, such that the intake tracking services of the app may be integrated with, for example, fitness tracking services of another application.

In the example embodiment, the user accesses the app or browser via the user interface. The ITR computing device causes display of a prompt for the user to enter a nutritional- or intake-related objective. In some embodiments, the ITR computing device causes display of drop-down lists, text entry fields, buttons, other selection or entry fields, and/or combinations thereof for the user to select, set, edit, update, and/or define their own objective. The objective may be further associated with an interval of time (e.g., a day, a week, a month, and/or an irregular interval of time, such as "until my next grocery order"). For example, one nutritional objective may be defined by the user as "Consuming less than 128 g of saturated fat per week." The user defines one or more such nutritional objectives according to their personal health or dietary needs or goals.

The ITR computing device also receives user input of a user-defined reward. The reward is made accessible to the user upon the user's meeting of the nutritional objective. In some embodiments, the reward is an amount of funds made available to purchase a food or grocery item that does not meet the user's objective. For example, if the user's objective is associated with a maximum amount of saturated fat or sugar to be purchased (and, thereby, consumed), the reward may be $10 (or any other monetary amount) that may be used to purchase a high-fat or high-sugar grocery item. This is referred to as an "in-app" reward, as the reward is accessible to the user through the same user interface with which the user interacts with the intake tracking services of the ITR computing device. The reward may additionally or alternatively be an amount of funds made accessible for a certain event, for a certain day, and/or at a certain time. For example, the user may define the reward to be $100 available on the following Friday night for a meal and/or entertainment. As described further herein, the $100 is made available to the user at a financial account associated with the user (e.g., a credit account or credit card, a debit account or debit card, a prepaid account or prepaid card, etc.), but not necessarily associated with the ITR computing device. Accordingly, these rewards are referred to as "out-of-app" rewards.

At a later time (e.g., directly after the user definition of the nutritional objective and/or at any other time), the ITR computing device causes display of a grocery ordering platform. The grocery ordering platform is displayed at the user interface for access by the user. The user may use the grocery ordering platform to make various grocery- or food-related purchases (e.g., to be delivered directly to their home). In some embodiments, the grocery ordering platform is associated with or interfaces with a grocery service (computing device) unaffiliated with the ITR computing device or the IOA system. In other embodiments, the IOA system includes and/or is otherwise affiliated with the grocery service. The ITR computing device receives the user input of a grocery order of one or more grocery items via the user interface.

The ITR computing device may transmit the order details (e.g., the items ordered, delivery date, address, etc.) to the grocery service. In one embodiment, the ITR computing device is configured to communicate with the one or more grocery service through a cloud-based Application Programming Interface (API). The API enables communication with any number of grocery services through the ITR computing device and/or through the app. The API may enable the user to access and interact with certain features of the grocery service(s) through the app, including making mobile payments directly to the grocery service.

The ITR computing device retrieves nutritional information associated with the grocery item(s) in the grocery order from the database. In particular, the ITR computing device retrieves nutritional information of the grocery item(s) that is associated with the user-defined intake objective. For example, if the user has set an objective to eat less than a particular amount of a particular nutrient (e.g., saturated fat or sodium), the ITR computing device retrieves the nutritional information of that nutrient present in the grocery items in the grocery order. As one example, the user orders three grocery items: a first, second, and third grocery item. The ITR computing device retrieves the nutritional information therefor and determines that the first, second, and third grocery items contain 16 g, 35 g, and 22 g of saturated fat, respectively.

Subsequently, the ITR computing device compiles a nutritional profile for the user from the retrieved nutritional information. More specifically, the ITR computing device compiles the retrieved nutritional information, as associated with the user's intake objective, for grocery items ordered within the period of time defined by the objective. If the user set an objective to eat less than a particular amount of a nutrient within a particular period of time (e.g., a week or a month), the ITR computing device compiles and maintains a nutritional profile of the amount of that nutrient in the grocery items ordered. Continuing with the example above, the ITR computing device maintains a nutritional profile indicating that the user has ordered items with a total of 73 g of saturated fat. If the user makes another order of a fourth item that week (or within any period of time defined in the user's intake objective), the fourth item containing 7 g of saturated fat, the ITR computing device updates the nutritional profile to indicate that the user has ordered items with a total of 80 g of saturated fat.

In some embodiments, the ITR computing device is configured to divide a total amount of the nutrient into a plurality of "serving size" amounts. For example, the fourth item contains 7 g of saturated fat in total but includes two serving sizes of the product. Each serving size therefore includes about 3.5 g saturated fat. The ITR computing device may divide each item into serving sizes to more accurately reflect consumption (more than just purchasing). In such embodiments, the ITR computing device may prompt the user to indicate when they have consumed a serving of the item. The ITR computing device then adds the value of the serving size to the nutritional profile. In addition, in some embodiments, the ITR computing device is configured to maintain a "pantry" for the user including their purchased foods and associated nutritional information. Moreover, the ITR computing device may enable the user to enter "out-of-app" meals or foods into their nutritional profile, such that the ITR computing device may factor in the user's consumption outside of their personal pantry.

The ITR computing device compares the nutritional profile to the objective to determine whether the user has met the intake objective. Specifically, the ITR computing device compares the amount of the particular nutrient associated with the objective to the amount of the particular nutrient associated with the nutritional profile. Continuing with the above example, the ITR computing device compares the 80 g of saturated fat in the nutritional profile, associated with the grocery items purchased by the user, with the 128 g of saturated fat, as defined in the user's intake objective. The ITR computing device may perform this comparison at regular intervals to monitor a user's progress. For example, the ITR computing device may perform the comparison once per day, once per week, etc. The ITR computing device may additionally or alternatively perform the comparison after each grocery order made by the user through the user interface, after the nutritional profile has been compiled and/or updated. Additionally or alternatively, the ITR computing device may perform the comparison at any other time, for example, on demand (e.g., upon a progress report request from the user), and/or at the end of the period of time defined in the user's intake objective.

In the example embodiment, if the ITR computing device determines that the user has met the objective, the ITR computing device releases (or otherwise makes accessible) the user-defined reward to the user. If the reward is an in-app reward, the ITR computing device may make the in-app reward immediately available to the user. If the reward is an out-of-app reward, the ITR computing device is configured to transmit an instruction to a financial institution associated with the financial account of the user. The instruction includes a user-defined reward amount and/or any other user-defined parameters of the reward (e.g., a particular time at which the reward is to be made available, an interval of time for which the reward is to be made available, etc.). The instruction causes the financial institution to provide the reward to the user according the user-defined reward parameters.

In certain embodiments, the IOA system includes a network of ITR computing devices accessed by different users. In these embodiments, the users may compete against one another, as a further accountability measure incentivizing the users to meet their nutritional objectives. The users may be permitted to see other users' progress towards their objectives, but may not be permitted to see the details of the objectives. For example, a first user competing with a second user may be permitted to see that the second user is under 50% of a maximum-consumption intake objective (e.g., "consume less than X amount of X nutrient"), but may not be able to see the exact amount or the exact nutrient associated with that objective. In these embodiments, the ITR computing device may be configured to release a reward only to the user who has performed best in terms of meeting their nutritional objective. Additionally or alternatively, the ITR computing device may be configured to release partial rewards according to the relative rank of the users within a competing group (e.g., release 100% of a first user's reward to a first user that performed best, release 90% of a second user's reward to a second user that performed second best, etc.). In some embodiments, the ITR computing device enables a competition between users with the same nutritional objective, such that comparison between users' progress is simplified.

Each user may have a user profile maintained by the ITR computing device, the user profile including the user intake objectives, the user-defined rewards, the nutritional profile, and any active "competitions" in which the user is involved. In one embodiment, the user may be required to manually set up their user profile using the app, wherein "manually set up" includes filling in a number of fields with information associated with the user. Some of this information may include personal or health information (e.g., sex, weight, height, etc.), home address, payment card and/or financial account information, and/or other information. In one embodiment, at least some of the user profile may be imported from another source, such as from a health record from the user, for example, from the user's healthcare or health insurance provider and/or from a user profile associated with another application (e.g., a fitness application or a social media application). In addition, the ITR computing device may track and store analytics associated with the user's behavior with the app, such as purchasing frequency/intervals, preferred brands, nutritional trends, etc. The ITR computing device may develop a usage history associated with the user profile such that the ITR computing device may generate intelligent recommendations (e.g., shopping lists) for the user that accord with their actual item usage preference (e.g., brands, merchants, items).

In some embodiments, the user may use the app to generate a "smart grocery order." The user may manually add items to this smart grocery order. Additionally, the ITR computing device may use the usage history (e.g., a purchase frequency or purchase schedule) to determine that the user should purchase the item again and may add the item to the smart grocery order. The ITR computing device may make the smart grocery order available to the user through the app, such that the user may access the smart grocery order on a user computing device. Moreover, based on the usage history for the user, the ITR computing device may enhance the smart grocery order to include preferred merchant(s) and/or brand(s) associated with items on the list, wherein "preferred" may refer generally to those merchants/brands with the highest purchase frequency.

The ITR computing device may be further configured to recommend certain recipes to the user that would enable the user to meet their nutritional objective(s). The ITR computing device may access a recipe database (e.g., as part of an internal database and/or as part of an external database, such as a cloud-based recipe service) and determine one or more recipes that would align with or satisfy the user's nutritional objective(s). For example, for a user with a nutritional objective to consume less than a maximum amount of sodium, the ITR computing device may determine a number of recipes that, when prepared, include a low amount of sodium and/or include ingredients with low sodium levels. The ITR computing device may suggest (e.g., push, through the app) one or more of these recipes and/or offer to populate a smart grocery order with the ingredients necessary to complete that recipe.

In some embodiments, the ITR computing device is configured to receive active offers (e.g., coupons, rewards, loyalty programs, etc.) from the one or more grocery service(s) accessible through the app. The ITR computing device may retrieve the active offers and push them to the app, or the user may select an option that allows grocery services to push offers to the app directly, when the merchant is identified in a smart grocery order and/or on a particular "grocery service list" granting such permissions. In some embodiments, certain offers may be pushed to the user according to various characteristics of the offer, including time-sensitive offers (e.g., a certain discount available only for the next hour), inventory-sensitive offers (e.g., the grocery service desires to sell a certain amount of a particular product), and/or usage history-sensitive offers. The grocery service may not have direct access to a usage history of the user but may instead maintain an inventory of active offers, and the ITR computing device may direct to the grocery service an indication of which active offers are related to the user's usage history, such that the grocery service and/or the ITR computing device may push relevant offers to the user. The ITR computing device may additionally or alternatively be configured to identify certain items in a grocery order that have associated active offers (e.g., by color-coding certain items or by providing an identifier next to certain items that the user may select to view the associated offer).

In the example implementation, any information stored on the IOA system does not include any personally identifiable information (PII), but rather includes analyzed, anonymized, and/or aggregated data that does not specifically identify a consumer. In other implementations, where the IOA system may store PII, any stored PII is encrypted and/or otherwise secured. Moreover, in any implementations in which PII may be collected, the consumer from which the PII may be collected is provided an opportunity to agree to or deny collection of such data.

The methods and systems described herein may be implemented using computer programming or engineering techniques including computer software, firmware, hardware, or any combination or subset therefor. At least one of the technical problems addressed by this system includes: (i) inefficient and tedious intake tracking using conventional methods; (ii) tedious, complicated, and/or inconvenient product tracking using conventional smart refrigerators; and (iii) lack of accountability measures in current intake tracking systems.

The technical effect of the systems and methods described herein is achieved by performing at least one of the following steps: (a) receiving user input of a nutritional objective from a user via the user interface; (b) receiving user input of a grocery order including a plurality of grocery items via the user interface; (c) retrieving nutritional information associated with the plurality of grocery items; (d) compiling a nutritional profile for the user from the retrieved nutritional information; (e) comparing the nutritional profile to the nutritional objective to determine whether the user has met the nutritional objective; and (f) releasing, when the user has met the nutritional objective, a reward to the user.

The resulting technical effect achieved by the systems and methods described herein is at least one of: (i) convenient and efficient tracking of a user's nutritional intake; (ii) improved product and nutritional tracking based directly on a user's food purchases without the need for additional input from the user; and (iii) built-in accountability measures designed to encourage a user to meet their goals using positive reinforcement. These solutions are necessarily tied to a computing device, specifically the specialized ITR computing device described herein, which may be embodied in a smart refrigerator. The automatic nutritional tracking services require the input of an electronic grocery order from a user, and the reward releases require (i) communication with a financial entity, and/or (ii) the user interface functionality to make available particular products.

In one embodiment, a computer program is provided, and the program is embodied on a computer-readable medium. In an example embodiment, the IOA system is executed on a single computer system, without requiring a connection to a sever computer. In a further example embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of AT&T located in New York, N.Y.). The application is flexible and designed to run in various different environments without compromising any major functionality. In some embodiments, the IOA system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

The following detailed description illustrates embodiments of the disclosure by way of example and not by way of limitation. It is contemplated that the disclosure has general application to processing purchase patterns in industrial, commercial, and residential applications.

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

FIG. 1 is a block diagram of an intake objective accountability (IOA) system 100 including an intake tracking and reward (ITR) computing device 102. ITR computing device 102 includes at least one processor in communication with a memory. ITR computing device 102 is in communication with a database (memory) 104 containing information on a variety of matters, including user intake objectives, user-defined rewards, nutritional information associated with grocery items (i.e., food items), grocery order information, usage history, competition information, and/or any other information. ITR computing device 102 is illustrated in FIG. 1 as embodied in a smart refrigerator. However, in other embodiments, ITR computing device 102 is embodied on another smart appliance (e.g., an oven, a microwave, etc.) and/or a computing device integrated into and/or otherwise in communication with one or more components of a "smart kitchen" (e.g., a smart phone, tablet, desktop, laptop, and/or a dedicated "smart home" computing device). In one embodiment, database 104 is stored on ITR computing device 102. In any alternative embodiment, database 104 is stored remotely from ITR computing device 102 and may be non-centralized.

In the example embodiment, IOA system 100 further includes a plurality of client subsystems, also referred to as client systems or user computing devices 108. In one embodiment, user computing devices 108 are computers including a web browser, such that ITR computing device 102 is accessible to user computing devices 108 using the Internet. User computing devices 108 are interconnected to the Internet through many interfaces including a network, such as a local area network (LAN) and/or a wide area network (WAN), dial-in connections, cable modems, wireless-connections, and special high-speed ISDN lines. User computing devices 108 may be any device capable of interconnecting to the Internet including a mobile computing device, such as a laptop or desktop computer, a web-based phone (e.g., a "smartphone"), a personal digital assistant (PDA), a tablet or phablet, a fitness wearable device, a smart refrigerator or other web-connectable appliance, a "smart watch" or other wearable device, or other web-connectable equipment. Although two user computing devices 108 are shown in FIG. 1 for clarity, it should be understood that IOA system 100 may include any number of user computing devices 108.

IOA system 100 further includes a grocery service (computing device) 112, which may include a real or virtual point-of-sale (POS) device, an inventory computing device, or any other computing device capable of communicating with ITR computing device 102 for receiving grocery orders. In the example embodiment, grocery service 112 is associated with a grocery merchant (not shown). ITR computing device 102 may access grocery service 112 through a cloud-based interface or API. ITR computing device 102 is configured to communicate with grocery service 112 to access any virtual merchant capabilities of the grocery service (e.g., to place one or more grocery orders, for delivery and/or pick-up, from the grocery merchant). Although only one grocery service 112 is shown in FIG. 1 for clarity, it should be understood that ITR computing device 102 may be in communication with any number of grocery services 112.

In one embodiment, ITR computing device 102 is configured to communicate with a user computing device 108 associated with a user (not shown). User computing device 108 is configured to display an app, for example, at (virtual) user interface 110 (described further herein). In other embodiments, ITR computing device 102 is configured to display the app at in an integral (physical) user interface 106 (described further herein). The app may be stored in a cloud-based interface (not shown), which may include cloud storage capability as well as any cloud-based API that facilitates communicates between a user computing devices 108 and ITR computing device 102 and/or between grocery service (computing devices) 112. The user accesses the app to access the intake tracking services of ITR computing device 102, as well as to make grocery orders from grocery services 112. The app stores a user profile associated with the user. The user profile includes user intake objectives, the user-defined rewards, any "in-app" earned rewards available for use, the nutritional profile, and any active "competitions" in which the user is involved. The user profile may be viewed, accessed, and/or updated by ITR computing device 102 and/or user computing devices 108. In addition, at least one of user computing devices 108 may access grocery service 112 directly, using the app as an interface, to access the virtual merchant capabilities of grocery service 112. In some embodiments, the app may have inter-app integration functionality, such that the intake tracking services of the app may be integrated with, for example, fitness tracking services of another application.

In the illustrated embodiment, ITR computing device 102 includes a front face or front wall 120 and at least two side faces or side walls 122 (only one of which is shown in FIG. 1). Front wall 120 includes a first door 124 and a second door 126. First door 124 may be a door to a refrigerator section (not shown), and second door 126 may be a door to a freezer section (not shown) of ITR computing device 102. It should be understood that a variety of other door configurations are contemplated within the scope of the disclosure, including fewer doors or more doors, drawer faces rather than hinges doors, etc. For example, ITR computing device 102 may include a three-door configuration featuring two "French doors" and a freezer drawer.

At least one of first door 124 and second door 126 includes the user interface 106 built into the door. User interface 106 may include touch screen functionality. In some embodiments, user interface 106 may be built into one of side walls 122. Moreover, in some embodiments, ITR computing device 102 may include more than one user interface 106 and/or other input/output components (e.g., a keyboard).

In the illustrated embodiment, ITR computing device 102 is in communication with a payment network 114. Payment network 114 is configured to process financial transactions thereover. Payment network 114 is in communication with a plurality of financial institutions 116 (e.g., banks), although only one financial institution 116 is shown for clarity. Financial institution 116 maintains one or more financial accounts 118 associated with a user of a user computing device 108, such as a credit card account, debit account, or prepaid account. ITR computing device 102 transmits reward instructions to payment network 114 to release funds in an award amount to financial account 118 of the user, in an "out-of-app" reward situation. The instructions cause payment network 114 to transmit instructions to financial institution 116 to release funds in the award amount to financial account 118. In some embodiments, ITR computing device 102 is in direct communication with financial institution 116 and transmits the reward instructions directly thereto, without the intervention of payment network 114.

Figure 2:
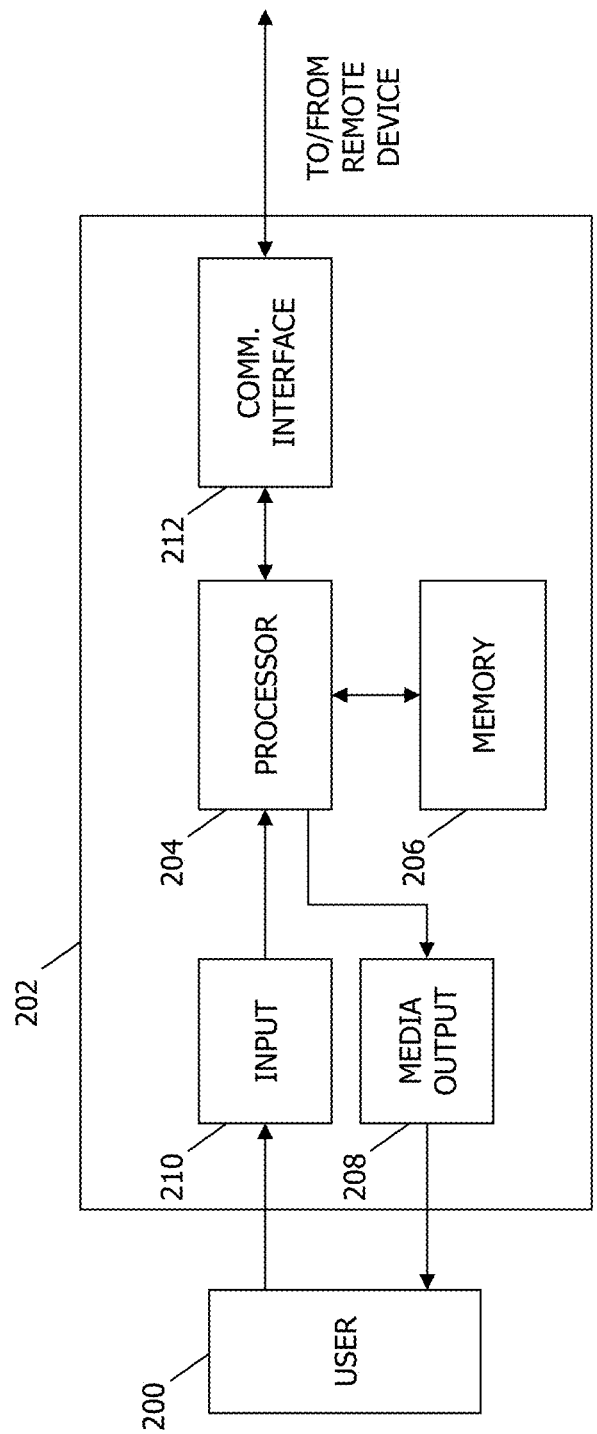

FIG. 2 illustrates an example configuration of a client computing device 202. Client computing device 202 may include, but is not limited to, client systems ("user computing devices") 108 and/or grocery services (computing devices) 112 (both shown in FIG. 1). Client computing device 202 includes a processor 204 for executing instructions. In some embodiments, executable instructions are stored in a memory area 206. Processor 204 may include one or more processing units (e.g., in a multi-core configuration). Memory area 206 is any device allowing information such as executable instructions and/or other data to be stored and retrieved. Memory area 206 may include one or more computer-readable media.

Client computing device 202 also includes at least one media output component 208 for presenting information to a user 200. Media output component 208 is any component capable of conveying information to user 200. In some embodiments, media output component 208 includes an output adapter such as a video adapter and/or an audio adapter. An output adapter is operatively coupled to processor 204 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, client computing device 202 includes an input device 210 for receiving input from user 200. Input device 210 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen (e.g., user interface 106, shown in FIG. 1) may function as both an output device of media output component 208 and input device 210.

Client computing device 202 may also include a communication interface 212, which is communicatively coupleable to a remote device such as ITR computing device 102 or a web server operated by a merchant (e.g., grocery service 112, both shown in FIG. 1). Communication interface 212 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 206 are, for example, computer-readable instructions for providing a user interface to user 200 via media output component 208 and, optionally, receiving and processing input from input device 210. A user interface may include, among other possibilities, a web browser and client application. Web browsers enable users 200 to display and interact with media and other information typically embedded on a web page or a website from a web server associated with a merchant. A client application allows users 200 to interact with a server application associated with, for example, a merchant and/or IOA system 100 (shown in FIG. 1).

Figure 3:
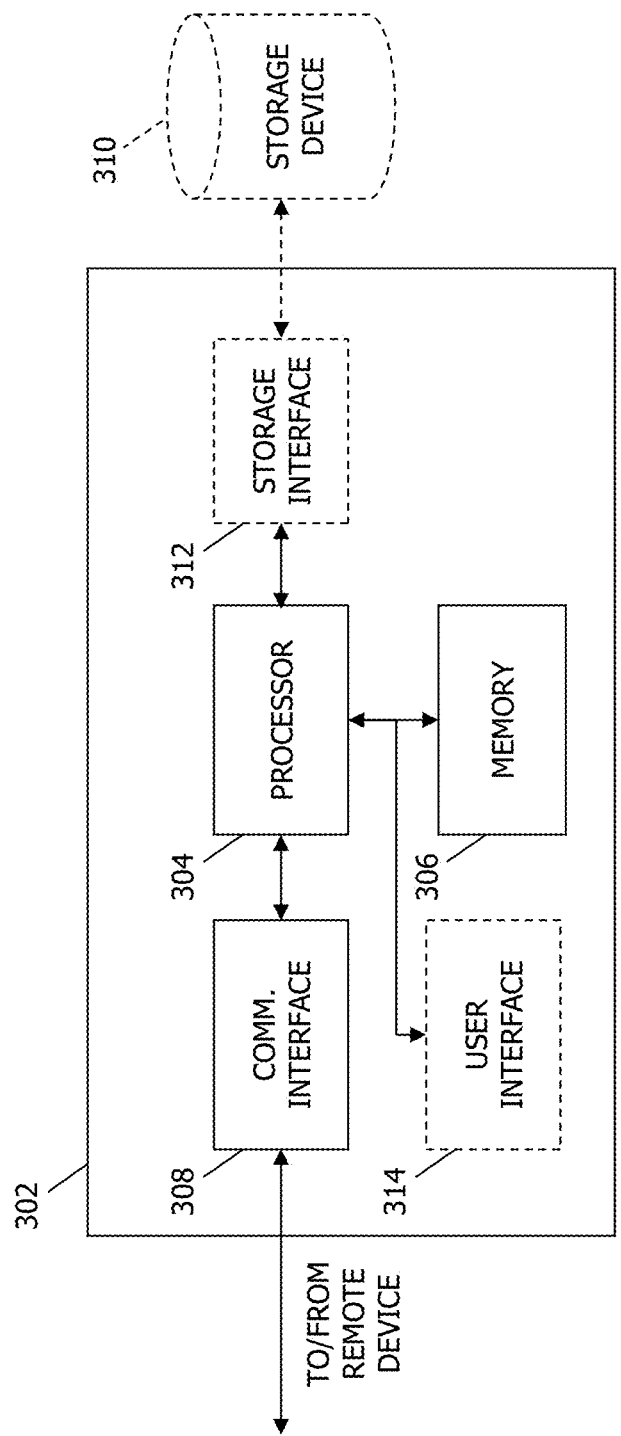

FIG. 3 illustrates an example configuration of a server computing device 302. Server computing device 302 may include, but is not limited to, ITR computing device 102, grocery service (computing device) 112, payment network 114 (all shown in FIG. 1). Server computing device 302 includes a processor 304 for executing instructions. Instructions may be stored in a memory area 306, for example. Processor 304 may include one or more processing units (e.g., in a multi-core configuration).

Processor 304 is operatively coupled to a communication interface 308 such that server computing device 302 is capable of communicating with a remote device such as client computing device 202 or another server computing device 302. For example, communication interface 308 may receive requests from user computing devices 108 via the Internet, as illustrated in FIG. 1.

Processor 304 may also be operatively coupled to a storage device 310. Storage device 310 is any computer-operated hardware suitable for storing and/or retrieving data. In some embodiments, storage device 310 is integrated in server computing device 302. For example, server computing device 302 may include one or more hard disk drives as storage device 310. In other embodiments, storage device 310 is external to server computing device 302 and may be accessed by a plurality of server computing devices 302. For example, storage device 310 may include multiple storage units such as hard disks or solid state disks in a redundant array of inexpensive disks (RAID) configuration. Storage device 310 may include a storage area network (SAN) and/or a network attached storage (NAS) system.

In some embodiments, processor 304 is operatively coupled to storage device 310 via a storage interface 312. Storage interface 312 is any component capable of providing processor 304 with access to storage device 310. Storage interface 312 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 304 with access to storage device 310.

Memory areas 306 and 206 (shown in FIG. 2) may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

In some embodiments, such as when server computing device 302 includes ITR computing device 102, server computing device 302 includes a (physical) user interface 314. User interface 314 may be similar to user interface 106 (shown in FIG. 1). User interface 314 may include any suitable interface components, including, for example, an input component (e.g., a touch screen, keyboard, mouse, input buttons, etc.) and an output component (e.g., a touch screen, a monitor, one or more indicator lights, etc.).

Figure 4:
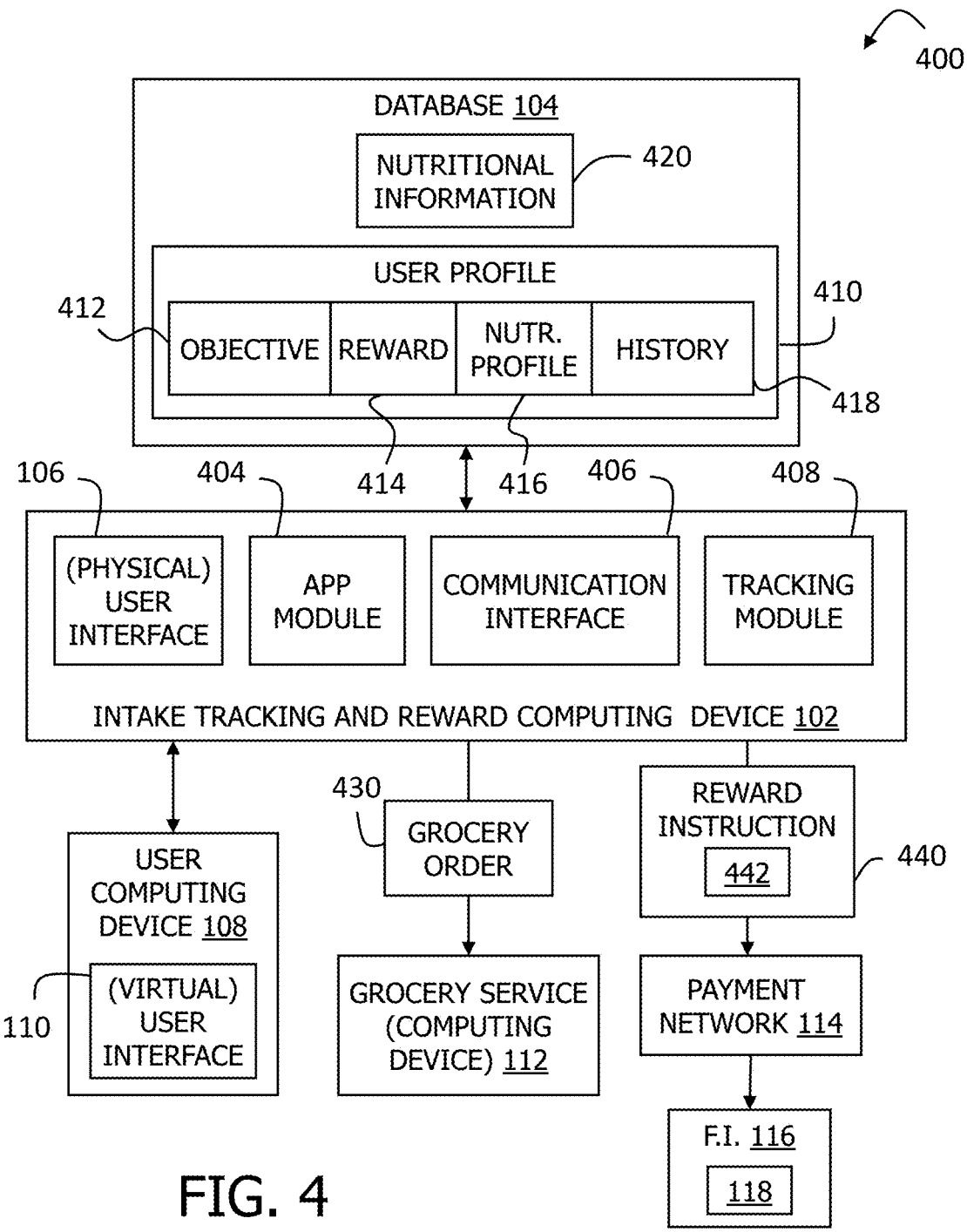

FIG. 4 is a data flow diagram 400 illustration the flow of various data between components of IOA system 100 (shown in FIG. 1). In the illustrated embodiment, as described above with respect to FIG. 1, ITR computing device 102 is in communication with database 104, user computing device 108, grocery service (computing device) 112, and payment network 114 (e.g., a payment processor). Although database 104 is illustrated as a separate and external component, it should be understood that, in an alternative embodiment, database 104 is a centralized database integral to ITR computing device 102.

In the illustrated embodiment, ITR computing device 102 is configured to receive user input of an intake or nutritional objective 412, track any grocery or food-related purchases made by the user through user interface 106/110, compare nutritional information 420 of the food-related purchases made to nutritional objective 412, and release a reward 414 to the user if the user meets nutritional objective 412. More particularly, a user of user computing device 108 accesses one of a (virtual) user interface 110 at user computing device 108 "paired with" or otherwise in communication with ITR computing device 102 and (physical) user interface 106 at ITR computing device 102. User interface 106 at ITR computing device 102 includes any kind of physical user interface, such as, for example, a touch screen configured to display a graphical user interface (GUI). In the example embodiment, ITR computing device 102 is integral to a smart refrigerator, such that user interface 106 is both a physical interface mounted on the smart refrigerator and a GUI displayed on the smart refrigerator. ITR computing device 102 includes an app module 404 configured to maintain and make available a software application ("app") at user interface 106 and/or user interface 110. App module 404 may be further configured to maintain a browser-accessible website. User interface 110 at user computing device 108 refers to a GUI displayed on a physical user interface (not shown) of user computing device 108, for example, within the app maintained by app module 404. In other words, a user can access the functionality of ITR computing device 102 physically at ITR computing device 102 through user interface 106 and/or remotely with user computing device 108 through displayed user interface 110 (e.g., within an app). The user accesses the app as described above to, among other things, input a nutritional objective 412 (see FIG. 5), define a reward 414 (see FIG. 6), place a grocery order 430 (see FIG. 7), view their "pantry" of grocery items (FIG. 8), and view their progress towards their objective 412 (see FIG. 9), In some embodiments, the app may have inter-app integration functionality, such that the intake tracking services of ITR computing device 102 may be integrated with, for example, fitness tracking services of another application.

In the illustrated embodiment, ITR computing device 102 includes user interface 106, app module 404, a communication interface 406, and a tracking module 408. Communication interface 406 enables communication between ITR computing device 102 and at least one of user computing device 108, grocery service 112, and payment network 114. Tracking module 408 is configured to track a user's progress towards their nutritional objectives 412, as described further herein. App module 404 and tracking module 408 may be embodied as computer-executable instructions configured for execution by ITR computing device 102, for example, using a processor (e.g., processor 304, shown in FIG. 3). Alternatively, app module 404 and/or tracking module 408 may be executed on separate processing components. It should be understood that ITR computing device 102 may include fewer, more, and/or alternative modules.

Additionally, ITR computing device 102 includes and/or is in communication with database 104, such that ITR computing device 102 may store information on database 104 and/or access information previously stored thereon. In the illustrated embodiment, database 104 stores at least nutritional information 420 associated with grocery items (i.e., food items) and information associated with a user profile 410, such as user intake objectives 412, user-defined rewards 414, a nutritional profile 416 associated with a user, and a user's history 418 (which may include past grocery orders, a record of achieved/not-achieved goals, and/or other information, as described further herein). Database 104 may store additional and/or alternative information, such as grocery order information, and/or any other information.

Figure 5:
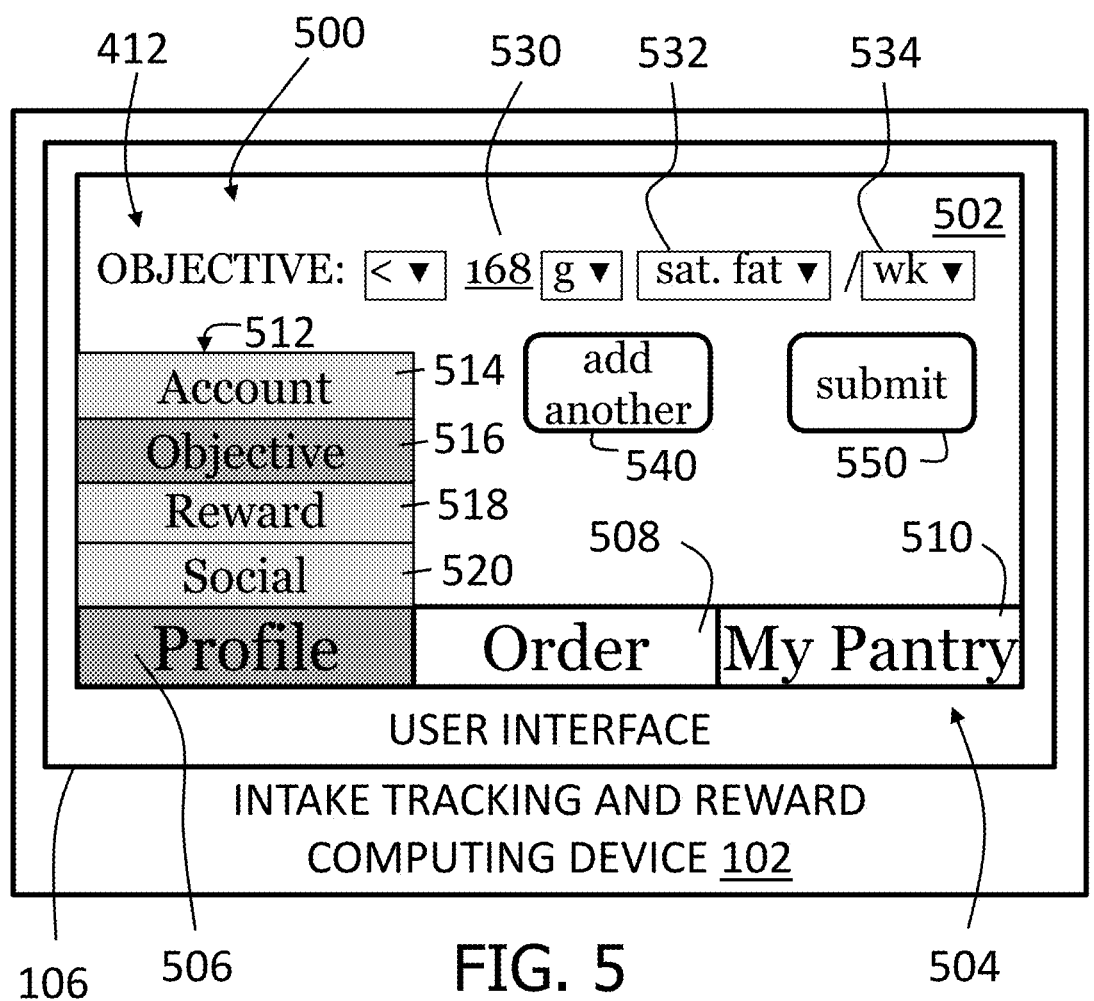

With reference to both FIGS. 4 and 5, one embodiment of the app is shown generally at 500. App 500 is displayed on user interface 106 of ITR computing device 102. Alternatively, app 500 is displayed on a user interface 110 of user computing device 108 (shown in FIG. 1). A screenshot 502 illustrates entry by a user of a nutritional objective 412. As shown, app 500 includes a menu of icons 504 that the user may interact with, including a "Profile" icon 506, an "Order" icon 508, and a "My Pantry" icon 510. Although three icons 506, 508, 510 are illustrated, it should be understood that there may be any number of icons in various alternative embodiments of app 500. Screenshot 502 illustrates a situation in which "Profile" icon 506 has been selected, which causes display of a profile sub-menu 512. The profile sub-menu 512 includes selectable links to additional pages and features associated with user profile 410. In the illustrated embodiments, those links include a link 514 to an "account" screen (e.g., for viewing contact information and/or basic information such as age and gender, for syncing information from app 500 with another application, etc.), a link 516 to an "objective" screen as shown in screenshot 502 (e.g., for inputting nutritional objective 412), a link 518 to a "reward" screen (e.g., for inputting user-defined reward 414), and a link 520 to a "social" screen (e.g., for setting up and/or viewing competitions).

In addition, one of links 514, 516, 518, 520 and/or additional/alternative links may enable the user to access other features of their user profile 410. In one embodiment, the user may be required to manually set up their user profile 410 using app 500, wherein "manually set up" includes filling in a number of fields with information associated with the user. Some of this information may include personal or health information (e.g., sex, weight, height, etc.), home address, payment card and/or financial account information, and/or other information. In one embodiment, at least some of user profile 410 may be imported from another source, such as from a health record from the user, for example, from the user's healthcare or health insurance provider and/or from a user profile associated with another application (e.g., a fitness application or a social media application). In addition, ITR computing device 102 (e.g., tracking module 408) may track and store analytics associated with the user's behavior with app 500, such as purchasing frequency/intervals, preferred brands, nutritional trends, etc. Tracking module 408 may accordingly develop a usage history 418 associated with user profile 410 such that the tracking module 408 may generate intelligent recommendations (e.g., shopping lists) for the user that accord with their actual item usage preference (e.g., brands, merchants, items). In some embodiments, one link from profile sub-menu 512 many enable the user to sync or pair their user profile 410 on app 500 with additional user computing device(s) 108, including, for example, a fitness wearable, and/or with ITR computing device 102 or a smart refrigerator.

The objective screen enables a user to input their nutritional objective 412. As illustrated in screenshot 502, app module 404 may facilitate display of a plurality of controls for the user to manipulate to select, set, edit, update, and/or define their own objective 412, including drop-down menus and text entry fields. Additional and/or alternative controls may be available, such as radio buttons, check boxes, and/or other controls. Each objective 412 is associated with at least one value 530, for example, a minimum or maximum amount, and with at least one nutrient 532, such as a macronutrient, vitamin, mineral, or calories. Each objective 412 may be further associated with an interval of time 534 (e.g., a day, a week, a month, and/or an irregular interval of time, such as "until my next grocery order"). For example, the illustrated nutritional objective 412 is defined by the user as "Consuming less than 128 g of saturated fat per week." The user may select an "add another" command 540 to define an additional nutritional objective 412, according to their own personal health or dietary needs/goals. The user may select a "submit" command 550 to submit the one or more nutritional objectives 412 for tracking by ITR computing device 102. ITR computing device 102 receives the nutritional objective(s) 412 and, in one example embodiment, stores them in database 104.

Figure 6:
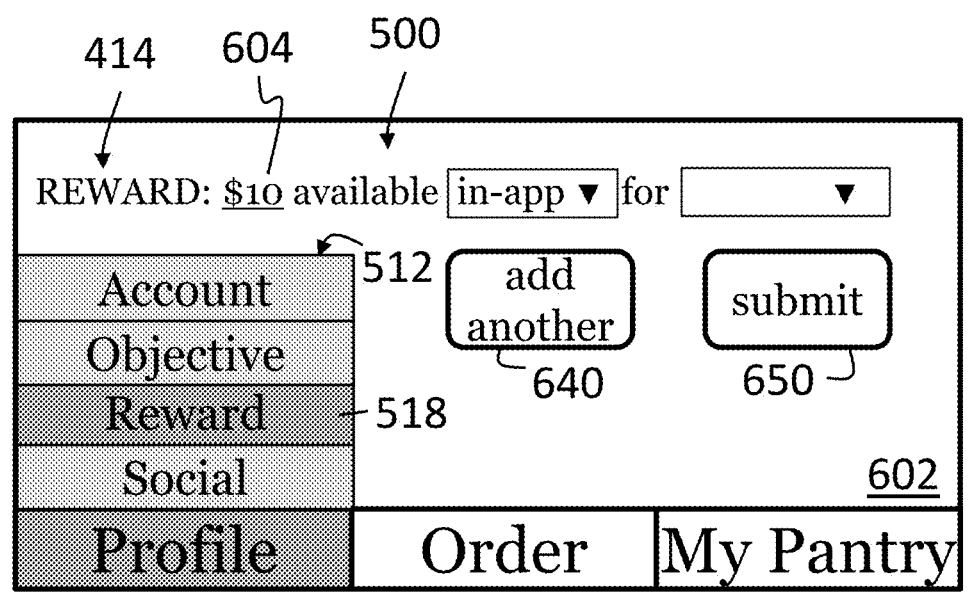

With reference now to FIGS. 4 and 6, a screenshot 602 illustrates entry of a user-defined reward 414. In screenshot 602, the link 518 in the profile sub-menu 512 has been selected by a user, such that a reward screen is accessed. The reward screen enables a user to define and input their reward 414, which is made accessible to the user upon the user's meeting of a nutritional objective 412. As illustrated in screenshot 602, app module 404 may facilitate display of a plurality of controls for the user to manipulate to select, set, edit, update, and/or define their own reward 414, including drop-down menus and text entry fields. Additional and/or alternative controls may be available, such as radio buttons, check boxes, and/or other controls. In some embodiments, reward 414 is an amount of funds 604 made available to purchase a food or grocery item that does not meet the user's nutritional objective 412. For example, if the user's nutritional objective 412 is associated with a maximum amount of saturated fat or sugar to be purchased (and, thereby, consumed), reward 414 may be $10 (or any other monetary amount 604) that may be used to purchase a high-fat or high-sugar grocery item. This is referred to as an "in-app" reward 414, as the reward 414 is accessible to the user through app 500, using the same user interface 106/110 with which the user interacts with the intake tracking services of ITR computing device 102.

A reward 414 may additionally or alternatively be an amount of funds 604 made accessible for a certain event, for a certain day, and/or at a certain time. For example, the user may define reward 414 to be $100 available on the following Friday night for a meal and/or entertainment. If the user meets their nutritional objective 412, the $100 is made available to the user at a financial account 118 (shown in FIG. 1) associated with the user (e.g., a credit account or credit card, a debit account or debit card, a prepaid account or prepaid card, etc.), but not necessarily associated with ITR computing device 102. Accordingly, these rewards 414 are referred to as "out-of-app" rewards 414. More specifically, payment network 114 is configured to implement enhanced authorization controls (e.g., via MasterCard® InControl®, registered trademarks for MasterCard International, Purchase, N.Y.) on financial account 118 such that the spending of reward 414 is limited according to the parameters of the out-of-app reward 414 set by the user (e.g., amount 604 available for spending, purchase type/merchant type, validity period of the reward amount, etc.).

The user may select an "add another" command 640 to define an additional or alternative reward 414, which may be associated with an additional or alternative nutritional objective 412. In some embodiments, the user may be able to define rewards 414 corresponding to different levels of success in achieving their objective(s) 412. For example, one smaller reward 414 may be defined for meeting 50% of a (minimum-consumption) objective 412 or being within 10% or 20% of a (maximum-consumption) objective 412; and one larger reward 414 may be defined for fully achieving objective 412. The user may select a "submit" command 650 to submit the one or more rewards 414 to ITR computing device 102. ITR computing device 102 receives reward(s) 414 and, in one example embodiment, stores them in database 104.

Figure 7:
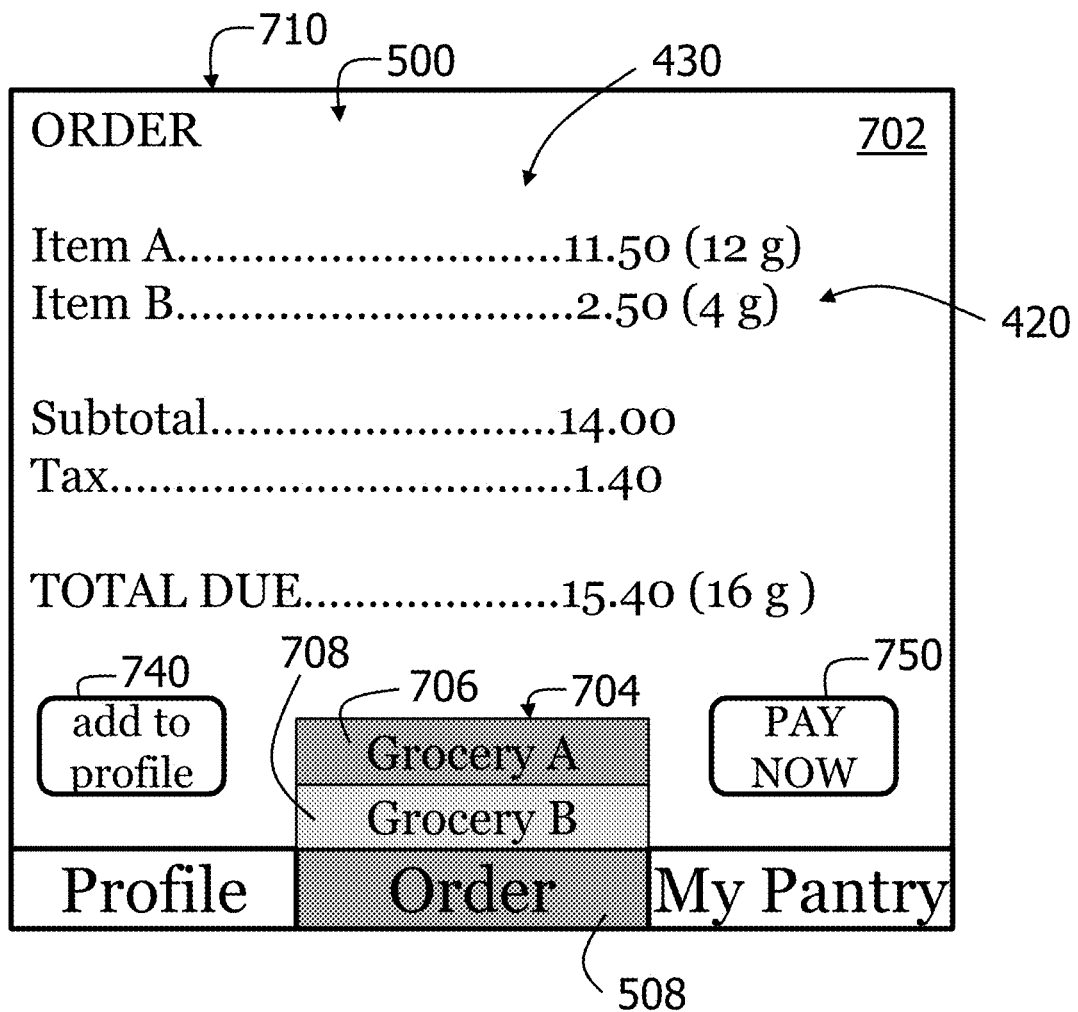

With reference now to FIGS. 4 and 7, a screenshot 702 illustrates a user initiating a grocery order 430 with grocery service 112 through app 500. In screenshot 702, Order icon 508 has been selected by a user. In the illustrated embodiment, selecting Order icon 508 causes an order sub-menu 704 to be displayed. Order sub-menu 704 includes a plurality of links 706, 708 to different grocery services 112. Upon selection of one of links 706, 708, app module 404 causes a grocery ordering platform 710 to be displayed. The user may use grocery ordering platform 710 to make various grocery- or food-related purchases (e.g., to be delivered directly to their home). In some embodiments, grocery ordering platform 710 is associated with or interfaces with a grocery service 112 unaffiliated with ITR computing device 102 or IOA system 100. In other embodiments, IOA system 100 includes and/or is otherwise affiliated with grocery service 112. In some embodiments, grocery ordering platform 710 is a GUI designed by grocery service 112, such that the user easily recognizes the particular grocery service 112 from whom they are ordering. In other embodiment, grocery ordering platform 710 appears the same no matter which grocery service 112 is selected (using links 706, 708).

Using grocery ordering platform 710, the user may find and select their desired grocery items for ordering. It should be understood that although reference is primarily made to food-related grocery items, grocery ordering platform 710 may facilitate ordering of any kind of products available through the grocery service, including household products, cleaning supplies, etc. ITR computing device 102 is configured to recognize non-food-related grocery items in a grocery order 430 and disregards these items in further processing. In screenshot 702, the user has selected two food-related grocery items for purchase (i.e., Item A and Item B) and added them to grocery order 430. In the illustrated embodiments, ITR computing device 102 has pre-populated nutritional information 420 associated with the items onto the order screen. More particularly, ITR computing device 102 has populated nutritional information 420 associated with the user's objective 412 for each item. In this way, a user may make informed decisions on the particular items they wish to purchase, and may make better intake choices based on the availability of the nutritional information 420 prior to making a purchase. In some embodiments, grocery service 112 and/or ITR computing device 102 may make nutritional information 420 available in other ways, such as via a link. In still other embodiments, ITR computing device 102 may "rank" items either in the user's grocery order 430 while the user is choosing between items to add to grocery order 430. For example, ITR computing device 102 may highlight items in a particular shade or color to indicate how well each item aligns with the user's nutritional objective 412.

Once the user has finished selecting their items for purchase, the user may select one of a "pay now" command 750 and an "add to profile" command 740. Selecting the "pay now" command 750 initiates transmitting the grocery order 430 to grocery service 112, as well as the tracking process of ITR computing device 102. Specifically, ITR computing device 102 receives grocery order 430 via user interface 106/110. In one embodiment, ITR computing device 102 acts as an intermediary for grocery order 430 and transmits grocery order 430 to grocery service 112 after parsing the grocery order 430 for item data (e.g., the items ordered, SKU numbers, brands, quantities, and/or additional information). ITR computing device 102 transmits the entirety of grocery order 430 (e.g., the items ordered, delivery date, address, etc.) to grocery service 112. In one embodiment, selection of the "pay now" command 750 further facilitates initiation of a bill-pay transaction from within app 500. For example, app 500 may include digital wallet functionality such that the user may pay for their grocery order 430 with their digital wallet or a payment card therein. Additionally or alternatively, app 500 may be communicatively coupled to an independent digital wallet application (not shown). In such cases, selection of the "pay now" command 750 may navigate the user to the digital wallet application, where the user may complete their bill-pay transaction. In one embodiment, ITR computing device 102 is configured to communicate with grocery service 112 through a cloud-based Application Programming Interface (API). The API may enable the user to access and interact with certain features of grocery service 112 through app 500, including making mobile payments directly to grocery service 112.

Based on the item data parsed from grocery order 730, ITR computing device 102 identifies the grocery items purchased. ITR computing device 102 retrieves nutritional information 420 associated with the grocery items from database 104. In particular, ITR computing device 102 retrieves nutritional information 420 of the grocery item(s) that is associated with the user's nutritional objective 420. For example, if the user has set an objective 412 to eat less than a particular amount of a particular nutrient 532 (e.g., saturated fat or sodium), ITR computing device 102 retrieves nutritional information 420 of that nutrient present in the grocery items. As described above, ITR computing device 102 may alternatively or additionally retrieve nutritional information 420 while a user is populating grocery order 430.

Subsequently, ITR computing device 102 automatically compiles a nutritional profile 416 for the user from retrieved nutritional information 420. More specifically, tracking module 408 of ITR computing device 102 compiles nutritional information 420 as associated with the user's nutritional objective 412, for grocery items ordered within the period of time 534 defined in objective 412. If the user set an objective 412 to eat less than a particular amount 530 of a nutrient 532 within a particular period of time 534 (e.g., a week or a month), tracking module 408 compiles and maintains nutritional profile 416 identifying the amount of that nutrient 532 in the grocery items ordered. Based upon the items shown in screenshot 702, tracking module 408 maintains nutritional profile 416 indicating that the user has ordered items with a total of 16 g of a nutrient 532 associated with their nutritional objective 412. If the user makes another order of another item that week (or within any period of time 534 defined in the user's objective 412), the next item containing 7 g of the nutrient 532, tracking module 408 would update nutritional profile 416 to indicate that the user has ordered items with a total of 23 g of the nutrient 532.

In some embodiments, tracking module 408 is configured to divide a total amount of the nutrient 532 into a plurality of "serving size" amounts. For example, if one item contains 7 g of the nutrient 532 in total but includes two serving sizes of the product, each serving size therefore includes about 3.5 g of the nutrient 532. Tracking module 408 may divide each item into serving sizes to more accurately reflect consumption (more than just purchasing). In such embodiments, tracking module 408 may prompt the user to indicate when they have consumed a serving of the item. Tracking module 408 then adds the value of the nutrient 532 in the serving size to nutritional profile 416. Additionally or alternatively, tracking module 408 may leverage the "scan" functionality of a smart refrigerator, in which the user may scan in and out various items as they are used/consumed. In some embodiments, tracking module 408 and/or app module 404 may enable a user to manually edit their nutritional profile 416, for example, by adding foods consumed outside of app 500. Tracking module 408 may retrieve nutritional information 420 of those added food items and update nutritional profile 416 accordingly.

In the example embodiment, selecting the "add to profile" command 740 transmits a pseudo-request to ITR computing device 102 to temporarily or unofficially add the selected items (e.g., items in a "cart") to the user's profile 410. In this embodiment, the user may see substantially immediately (and without finalizing a purchase) how buying the selected items would impact their nutritional profile 416, specifically their progress towards their nutritional objective 412. Tracking module 408 receives the pseudo-request and processes the selected items in the same way as if it had received a grocery order 430, described above. In one embodiment, tracking module 408 generates a temporary nutritional profile (not shown) including the existing, "official" nutritional profile 416 and nutritional information 420 of the selected items. Tracking module 408 may facilitate display of the temporary nutritional profile, for example, in a graphical manner illustrating progress towards nutritional objective 412. The user may then opt to complete grocery order 430 of the items, at which point tracking module 408 will update nutritional profile 416 accordingly.

In some embodiments, the user may use app 500 to generate a "smart grocery order" including items frequently purchases by the user. The user may manually add items to this smart grocery order. Tracking module 408 may use usage history 418 (e.g., a purchase frequency or purchase schedule) to determine that the user should purchase the item again (e.g., typically buys the item again at this frequency) and may add the item to the smart grocery order. Tracking module 408 may develop usage history 418 based upon past grocery orders 430. For example, tracking module 408 may maintain lists and/or tables of items purchased, time/date of purchase, grocery services 112 associated with each purchase, brands of item(s) purchased, and/or additional usage information. Tracking module 408 may make the smart grocery order available to the user through grocery ordering platform 710, such that the user may access the smart grocery order on a user computing device 108. Moreover, based on usage history 418 for the user, tracking module 408 may enhance the smart grocery order to include preferred merchant(s) and/or brand(s) associated with items on the list, wherein "preferred" may refer generally to those merchants/brands with the highest purchase frequency.

In some embodiments, ITR computing device 102 is configured to receive active offers (e.g., coupons, rewards, loyalty programs, etc.) from one or more grocery service(s) 112 accessible through app 500. Tracking module 408 may retrieve the active offers and push them to the use through app 500. Additionally or alternatively, the user may select an option within app 500 that allows grocery services 112 to push offers to app 500 directly, when the particular grocery service 112 is identified in a smart grocery order and/or on a particular "grocery service list" granting such permissions. In some embodiments, certain offers may be pushed to the user according to various characteristics of the offer, including time-sensitive offers (e.g., a certain discount available only for the next hour), inventory-sensitive offers (e.g., the grocery service 112 desires to sell a certain amount of a particular product), and/or usage history-sensitive offers. In the example embodiment, grocery service 112 may not have direct access to usage history 418 of the user but may instead maintain an inventory of active offers, and tracking module 408 may direct to grocery service 112 an indication of which active offers are related to the user's usage history 418, such that grocery service 112 and/or tracking module 408 may push relevant offers to the user. Tracking module 408 may additionally or alternatively be configured to identify certain items in a grocery order that have associated active offers (e.g., by color-coding certain items or by providing an identifier next to certain items that the user may select to view the associated offer).

In the example embodiment, if tracking module 408 determines that the user has met the objective, tracking module 408 releases (or otherwise makes accessible) user-defined reward 414 to the user. If reward 414 is an in-app reward, tracking module 408 may make in-app reward 414 immediately available to the user. If reward 414 is an out-of-app reward, tracking module 408 is configured to transmit a reward instruction 440 to financial institution 116 associated with financial account 118 of the user. Reward instruction 440 includes a user-defined reward amount (e.g., amount 604, shown in FIG. 6) and/or any other user-defined parameters 442 of reward 414 (e.g., a particular time at which reward 414 is to be made available, an interval of time for which reward 414 is to be made available, etc.). Reward instruction 440 causes financial institution 116 to provide reward 414 to the user according the user-defined reward parameters 442. In some embodiments, tracking module 408 transmits reward instruction 440 through payment network 114, which processes reward instruction 440 for the user-defined reward parameters 442 and imposes corresponding authorization controls on financial account 118 and/or a payment card associated therewith.

Figure 8:
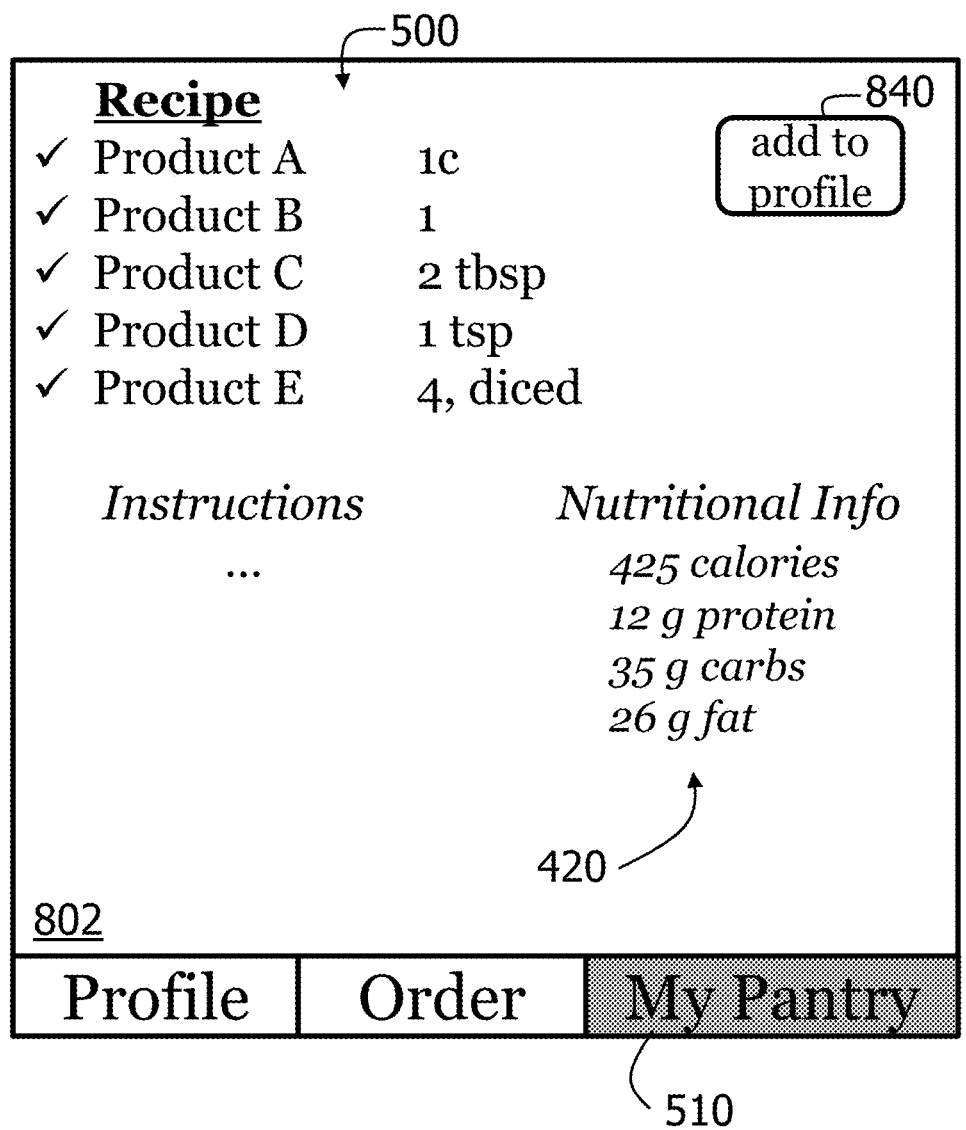

With additional reference now to FIG. 8, a screenshot 802 shows a pantry screen. In the example embodiment, the pantry screen is accessed when a user selects Pantry option 510. In some embodiments, tracking module 408 is configured to maintain a "pantry" for the user including their purchased foods and associated nutritional information 420. In such embodiments, tracking module 408 may leverage the "scan" functionality of a smart refrigerator, in which the user may scan in and out various items as they are used/consumed. In this way, tracking module 408 may track consumption and monitor how much of a particular product remains.

In some embodiments, tracking module 408 is further configured to recommend certain recipes to the user that would enable the user to meet their nutritional objective(s) 412. Tracking module 408 may access a recipe database (e.g., as part of database 104 and/or as part of an external database, such as a cloud-based recipe service, not shown) and determine one or more recipes that would align with or satisfy the user's nutritional objective(s) 412 and/or recipes that take advantage of grocery items purchased by the user through app 500 that remain in the user's pantry. For example, for a user with a nutritional objective 412 to consume less than a maximum amount of sodium, tracking module 408 may identify and retrieve a number of recipes that, when prepared, include a low amount of sodium and/or include ingredients with low sodium levels. Tracking module 408 may suggest (e.g., push, as a notification through app 500 or in an email or other electronic message) one or more of these recipes. In cases in which the user does not have all of the ingredients in their pantry, according to tracking module 408, tracking module 408 may offer to populate a smart grocery order with the ingredients necessary to complete that recipe.

In some embodiments, tracking module 408 and/or app module 404 may enable a user to manually edit their nutritional profile 416, for example, by adding foods consumed outside of app 500. Tracking module 408 may retrieve nutritional information 420 of those added food items and update nutritional profile 416 accordingly. For example, the user may select an "add to profile" command 840 to add the nutritional information 420 associated with a grocery item or recipe to their nutritional profile 416.

Figure 9:
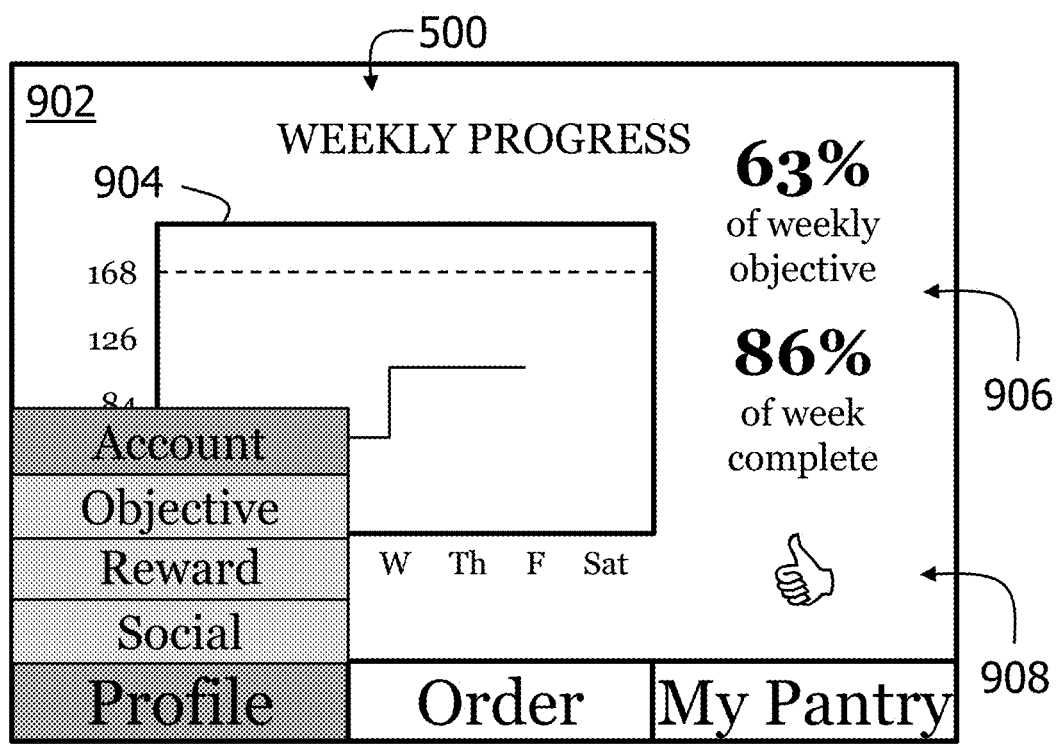

With reference now to FIGS. 4 and 9, a screenshot 902 shows a progress screen. Once nutritional profile 416 is developed, tracking module 408 compares nutritional profile 416 to objective 412 to determine whether the user has achieved objective 412. Specifically, tracking module 418 compares the amount of the particular nutrient 532 associated with objective 412 to the amount of the particular nutrient 532 associated with nutritional profile 416. Tracking module 408 may perform this comparison at regular intervals to monitor a user's progress. For example, tracking module 408 may perform the comparison once per day, once per week, etc. tracking module 408 may additionally or alternatively perform the comparison after each grocery order 430 made by the user through user interface 106/110, after nutritional profile 416 is compiled and/or updated. Additionally or alternatively, tracking module 408 may perform the comparison at any other time, for example, on demand (e.g., upon a progress report request from the user), and/or at the end of the period of time 534 defined in the user's nutritional objective 412.

Tracking module 408 communicates with app module 404 to display a graphical interpretation of a user's progress toward their nutritional objective 412. In the illustrated embodiment, tracking module 408 has formatted the user's progress as a graph or chart 904 as well as in a numerical format 906 and with a binary indicator 908. Binary indicator 908, illustrated as a "thumbs up", offers a simple at-a-glance indication regarding whether the user is performing well (e.g., "thumbs up", plus sign (+), upward arrow, etc.) or poorly (e.g., "thumbs down," minus sign (−), downward arrow, etc.). A user may input their preference for how they would like to receive their progress, which may be any format, such a table, chart, graph, set of values, and/or in any other format.

In certain embodiments, IOA system 100 includes a network of ITR computing devices 102 accessed by different users. In these embodiments, the users may compete against one another, as a further accountability measure incentivizing the users to meet their nutritional objectives 412. The users may be permitted to see other users' progress towards their objectives 412, but may not be permitted to see the details of the objectives 412. For example, a first user competing with a second user may be permitted to see that the second user is under 50% of a maximum-consumption intake objective 412 (e.g., "consume less than X amount of X nutrient"), but may not be able to see the exact amount 530 or the exact nutrient 532 associated with that objective 412. In these embodiments, ITR computing device 102 (e.g., tracking module 408) may be configured to release a reward 414 only to the user who has performed best in terms of meeting their nutritional objective 412. Additionally or alternatively, tracking module 408 may be configured to release partial rewards 414 according to the relative rank of the users within a competing group (e.g., release 100% of a first user's reward 414 to a first user that performed best, release 90% of a second user's reward 414 to a second user that performed second best, etc.). Additionally or alternatively, users may define competition-specific rewards, which may be additional rewards on top of their objective-specific rewards 414. In these cases, performing well in the competition adds to the amount of funds released when the competition is over, but performing poorly in the competition does not detract from the user meeting their own personal objective 412. In some embodiments, tracking module 408 enables a competition between users with the same nutritional objective 412, such that comparison between users' progress is simplified. The users may access the same progress page as shown in screenshot 902 and/or a different progress page to view their progress within each "active" competition.

Figure 10:
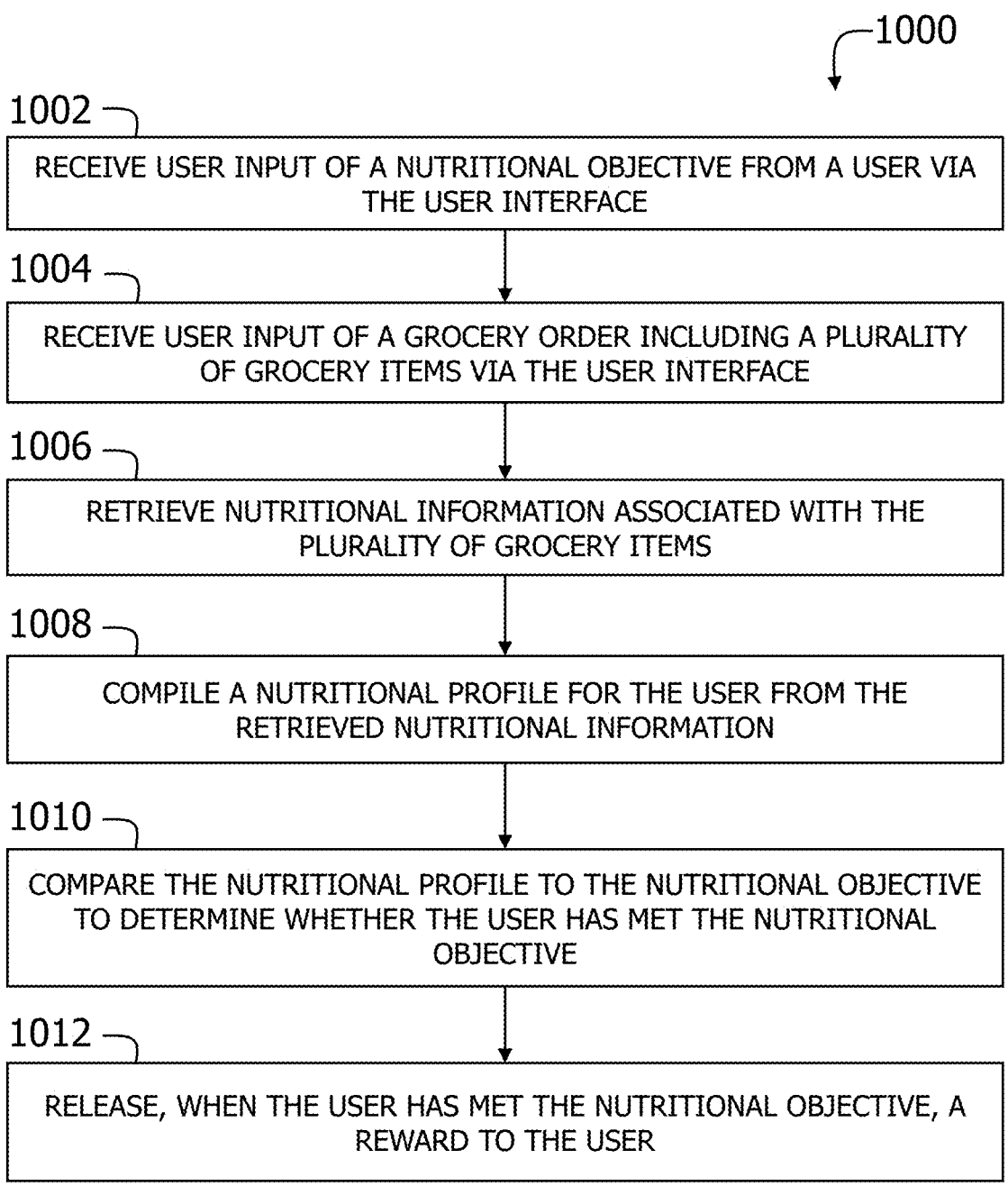

FIG. 10 is a flowchart of a method 1000 for implementing accountability measures associated with nutritional objectives. Method 1000 may be performed using ITR computing device 102 (shown in FIG. 1). Specifically, in one example embodiment, method 1000 is performed using a smart refrigerator (e.g., ITR computing device 102, embodied on a smart refrigerator).

Method 1000 includes receiving 1002 user input of a nutritional objective (e.g., nutritional objective 412, shown in FIG. 4) from a user via a user interface (e.g., user interface 106 and/or user interface 110, both shown in FIG. 1). Method 1000 also includes receiving 1004 user input of a grocery order (e.g., grocery order 430, shown in FIG. 4) including a plurality of grocery items via the user interface. Method 1000 further includes retrieving 1006 nutritional information (e.g., nutritional information 420, also shown in FIG. 4) associated with the plurality of grocery items.

Method 1000 also includes compiling 1008 a nutritional profile (e.g., nutritional profile 416, shown in FIG. 4) for the user from the retrieved nutritional information. Method 1000 still further includes comparing 1010 the nutritional profile to the nutritional objective to determine whether the user has met the nutritional objective, and releasing 1012, when the user has met the nutritional objective, a reward (e.g., reward 414, shown in FIG. 4) to the user. In the example embodiment, the reward is user-defined.

Figure 11:
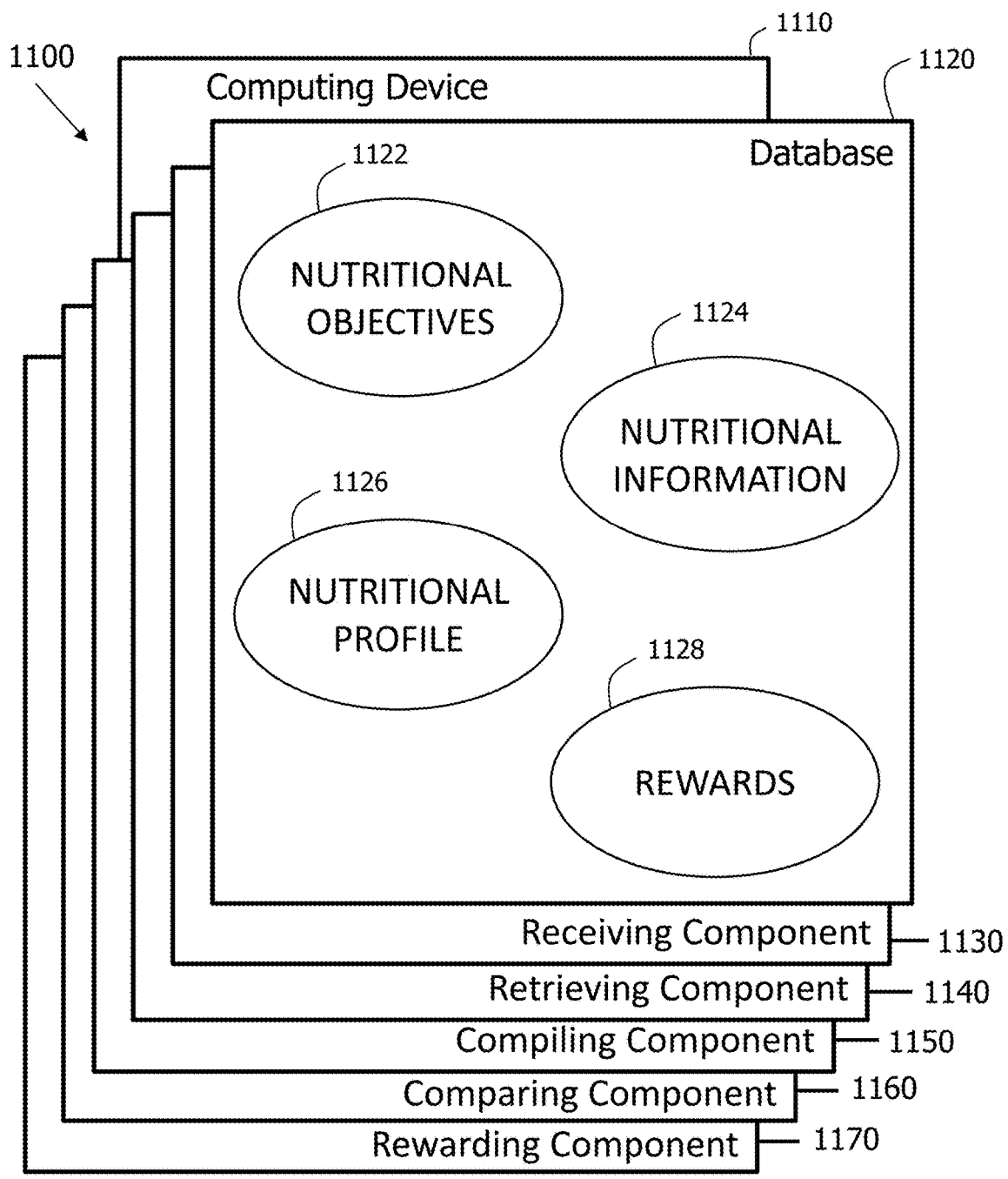

FIG. 11 is a diagram 1100 of components of an example computing device 1110 that may be used in the IOA system 100 shown in FIG. 1. In some embodiments, computing device 1110 is similar to ITR computing device 102 (shown in FIG. 1) and may include a smart refrigerator. Computing device 1110 includes a database 1120 configured to store various information. Database 1120 may be similar to database 104 (shown in FIG. 1). In the illustrated embodiment, database 1120 stores nutritional objectives 1122 (which may include and/or be similar to nutritional objectives 412, shown in FIG. 4), nutritional information 1124 (which may include and/or be similar to nutritional information 420, shown in FIG. 4), nutritional profiles 1126 (which may include and/or be similar to nutritional profiles 416, shown in FIG. 4), and rewards 1128 (which may include and/or be similar to rewards 414, shown in FIG. 4). Database 1120 may be coupled with several separate components within computing device 1110, which perform specific tasks.

In the example embodiment, computing device 1110 includes a receiving component 1130. Receiving component 1130 is configured to receive user input of a nutritional objective 1122 from a user via a user interface. Receiving component 1130 is further configured to receive user input of a grocery order including a plurality of grocery items via the user interface. Computing device 1110 also includes a retrieving component 1140, which is configured to retrieve nutritional information 1124 associated with the plurality of grocery items.

Computing device 1110 further includes a compiling component 1150. Compiling component 1150 is configured to compile a nutritional profile 1126 for the user from the retrieved nutritional information 1124. Computing device 1110 also include a comparing component 1160 configured to compare the nutritional profile 1126 to the nutritional objective 1122 to determine whether the user has met the nutritional objective 1122, and a rewarding component 1170 configured to release, when the user has met the nutritional objective, a reward 1128 to the user. Computing device 1110 may include fewer, more, and/or additional components, including transmitting, displaying, communication, and/or processing components.

The term processor, as used herein, refers to central processing units, microprocessors, microcontrollers, reduced instruction set circuits (RISC), application specific integrated circuits (ASIC), logic circuits, and any other circuit or processor capable of executing the functions described herein.

As used herein, the terms "software" and "firmware" are interchangeable, and include any computer program stored in memory for execution by processor 204, including RAM memory, ROM memory, EPROM memory, EEPROM memory, and non-volatile RAM (NVRAM) memory. The above memory types are example only, and are thus not limiting as to the types of memory usable for storage of a computer program.

As will be appreciated based on the foregoing specification, the above-discussed embodiments of the disclosure may be implemented using computer programming or engineering techniques including computer software, firmware, hardware or any combination or subset thereof. Any such resulting computer program, having computer-readable and/or computer-executable instructions, may be embodied or provided within one or more computer-readable media, thereby making a computer program product, i.e., an article of manufacture, according to the discussed embodiments of the disclosure. These computer programs (also known as programs, software, software applications or code) include machine instructions for a programmable processor, and can be implemented in a high-level procedural and/or object-oriented programming language, and/or in assembly/machine language. As used herein, the terms "machine-readable medium," "computer-readable medium," and "computer-readable media" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium," "computer-readable medium," and "computer-readable media," however, do not include transitory signals (i.e., they are "non-transitory"). The term "machine-readable signal" refers to any signal used to provide machine instructions and/or data to a programmable processor.

In addition, although various elements of the ITR computing device are described herein as including general processing and memory devices, it should be understood that the ITR computing device is a specialized computer configured to perform the steps described herein for implementing accountability measures by tracking a user's progress toward a nutritional objective and releasing a reward upon achievement of the objective.

This written description uses examples, including the best mode, to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A smart refrigerator comprising:
   a plurality of walls enclosing a refrigerated section;
   a memory;
   a user interface; and
   a processor in communication with said memory and said user interface, said processor programmed to:
     obtain from a user via the user interface a first set of rules that define a nutritional objective as a function of a grocery order and an interval of time for the grocery order;
     display, on the user interface, a grocery ordering platform;
     obtain, through the grocery ordering platform, user input of the grocery order having a plurality of grocery items;
     retrieve, while obtaining the user input of the grocery order, nutritional information associated with the plurality of grocery items;
     generate a temporary nutritional profile for the user based on the retrieved nutritional information for all of the plurality of grocery items and an existing nutritional profile representing one or more previous grocery orders within the interval of time;
     determine whether the user is likely to meet the nutritional objective by evaluating the temporary nutritional profile against the first set of rules;
     identify, based on the determining, at least one candidate grocery item of the plurality of grocery items that reduces the likelihood the user will meet the nutritional objective;
     visually highlight, on the grocery ordering platform, the at least one candidate grocery item;
     receive, through the grocery ordering platform, user input removing the at least one candidate grocery item from the grocery order;
     transmit the grocery order to a grocery merchant;
     update the existing nutritional profile for the user based on the transmitted grocery order;
     determine the user has met the nutritional objective by evaluating the updated nutritional profile against the first set of rules; and
     produce, based on the determining, a user-defined reward to the user.

2. The smart refrigerator of claim 1, wherein the user-defined reward includes access to one or more grocery items having associated nutritional information that does not meet the nutritional objective.

3. The smart refrigerator of claim 2, wherein said processor is further programmed to make the user-defined reward accessible to the user via the user interface.

4. The smart refrigerator of claim 1, wherein the user-defined reward includes an amount of money to purchase one or more grocery items having associated nutritional information that does not meet the nutritional objective.

5. The smart refrigerator of claim 1, wherein the user-defined reward includes access to an amount of reward funds.

6. The smart refrigerator of claim 5, wherein the reward funds are accessible for a predetermined period of time.

7. The smart refrigerator of claim 5, wherein the amount is predetermined by the user.

8. The smart refrigerator of claim 1, wherein said processor is further programmed to receive user input from the user of the user-defined reward via the user interface.

9. The smart refrigerator of claim 1, wherein the user is a first user, and wherein said processor is further programmed to:
   identify a plurality of users including the first user with the same nutritional objective;
   compare nutritional profiles associated with respective users of the plurality of users; and
   produce the user-defined reward upon determining that the nutritional profile of the first user best meets the nutritional objective.

10. A method for implementing accountability measures associated with nutritional objectives, said method performed using an intake tracking and reward (ITR) computing device including a plurality of walls enclosing a refrigerated section, a memory, a user interface, and a processor in communication with the memory and the user interface, said method comprising:
   obtaining from a user via the user interface a first set of rules that define a nutritional objective as a function of a grocery order and an interval of time for the grocery order;
   displaying, on the user interface, a grocery ordering platform;
   obtaining, through the grocery ordering platform, user input of the grocery order having a plurality of grocery items;
   retrieving, while obtaining the user input of the grocery order, nutritional information associated with the plurality of grocery items;
   generating a temporary nutritional profile for the user based on the retrieved nutritional information for all of the plurality of grocery items and an existing nutritional profile representing one or more previous grocery orders within the interval of time;
   determining whether the user is likely to meet the nutritional objective by evaluating the temporary nutritional profile against the first set of rules;
   identifying, based on the determining, at least one candidate grocery item of the plurality of grocery items that reduces the likelihood the user will meet the nutritional objective;
   visually highlighting, on the grocery ordering platform, the at least one candidate grocery item;

receiving, through the grocery ordering platform, user input removing the at least one candidate grocery item from the grocery order;

transmitting the grocery order to a grocery merchant;

updating the existing nutritional profile for the user based on the transmitted grocery order;

determining the user has met the nutritional objective by evaluating the existing nutritional profile against the first set of rules; and producing, based on the determining, a user-defined reward to the user.

11. The method of claim 10, wherein releasing a user-defined reward to the user comprises releasing the reward including access to one or more grocery items having associated nutritional information that does not meet the nutritional objective.

12. The method of claim 11 further comprising making the user-defined reward accessible to the user via the user interface.

13. The method of claim 10, wherein releasing a user-defined reward to the user comprises releasing the reward including an amount of money to purchase one or more grocery items having associated nutritional information that does not meet the nutritional objective.

14. The method of claim 10, wherein releasing a user-defined reward to the user comprises releasing the user-defined reward including an amount of reward funds, wherein the reward funds are accessible for a predetermined amount of time and the amount is predetermined by the user.

15. The method of claim 10, wherein the user is a first user, said method further comprising:
identifying a plurality of users including the first user with the same nutritional objective;
comparing nutritional profiles associated with respective users of the plurality of users; and
producing the reward upon determining that the nutritional profile of the first user best meets the nutritional objective.

16. A non-transitory computer-readable storage medium having computer-executable instructions embodied thereon, wherein when executed by an intake tracking and rewards (ITR) computing device including a plurality of walls enclosing a refrigerated section and at least one processor coupled to a memory and a user interface, the computer-executable instructions cause the ITR computing device to:
obtain from a user via the user interface a first set of rules that define a nutritional objective as a function of a grocery order and an interval of time for the grocery order;
display, on the user interface, a grocery ordering platform;
obtain, through the grocery ordering platform, user input of the grocery order having a plurality of grocery items;
retrieve, while obtaining the user input of the grocery order, nutritional information associated with the plurality of grocery items;
generate a temporary nutritional profile for the user based on the retrieved nutritional information for all of the plurality of grocery items and an existing nutritional profile representing one or more previous grocery orders within the interval of time;
determine whether the user is likely to meet the nutritional objective by evaluating the temporary nutritional profile against the first set of rules;
identify, based on the determining, at least one candidate grocery item of the plurality of grocery items that reduces the likelihood the user will meet the nutritional objective;
visually highlight, on the grocery ordering platform, the at least one candidate grocery item;
receive, through the grocery ordering platform, user input removing the at least one candidate grocery item from the grocery order;
transmit the grocery order to a grocery merchant;
update the existing nutritional profile for the user based on the transmitted grocery order;
determine the user has met the nutritional objective by evaluating the updated nutritional profile against the first set of rules; and
produce, based on the determining, a user-defined reward to the user.

17. The non-transitory computer-readable storage claim 16, wherein the user-defined reward includes access to one or more grocery items having associated nutritional information that does not meet the nutritional objective.

18. The non-transitory computer-readable storage claim 16, wherein the user-defined reward includes an amount of money to purchase one or more grocery items having associated nutritional information that does not meet the nutritional objective.

19. The non-transitory computer-readable storage claim 16, wherein the user-defined reward includes an amount of reward funds, wherein the reward funds are accessible for a predetermined amount of time and the amount is predetermined by the user.

20. The smart refrigerator of claim 1, wherein said processor is further programmed to transmit an instruction to a financial institution associated with a financial account of the user to cause the financial institution to provide the user-defined reward to the user.

* * * * *